United States Patent
Ito

(10) Patent No.: US 11,871,905 B2
(45) Date of Patent: Jan. 16, 2024

(54) GASTRO-INTESTINAL-TRACT ABLATION SYSTEM

(71) Applicant: OLYMPUS CORPORATION, Tokyo (JP)

(72) Inventor: Ryosuke Ito, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 730 days.

(21) Appl. No.: 17/064,843

(22) Filed: Oct. 7, 2020

(65) Prior Publication Data
US 2021/0030262 A1 Feb. 4, 2021

Related U.S. Application Data

(63) Continuation of application No. PCT/JP2018/016143, filed on Apr. 19, 2018.

(51) Int. Cl.
*A61B 1/00* (2006.01)
*A61B 1/018* (2006.01)
(Continued)

(52) U.S. Cl.
CPC .......... *A61B 1/018* (2013.01); *A61B 1/00087* (2013.01); *A61B 1/00135* (2013.01);
(Continued)

(58) Field of Classification Search
CPC . A61B 1/00087; A61B 1/018; A61B 1/00135; A61B 2018/0022; A61B 2018/00494; A61B 2018/00982
See application file for complete search history.

(56) References Cited

U.S. PATENT DOCUMENTS 6,352,503 B1 3/2002 Matsui et al.
2003/0216613 A1 11/2003 Suzuki et al.
(Continued)

FOREIGN PATENT DOCUMENTS

EP 2368482 A1 9/2011
JP 2000-033071 A 2/2000
(Continued)

OTHER PUBLICATIONS

International Search Report dated Jul. 10, 2018 issued in PCT/JP2018/016143.

*Primary Examiner* — Timothy J Neal
(74) *Attorney, Agent, or Firm* — Scully, Scott, Murphy & Presser, P.C.

(57) ABSTRACT

An ablation system includes: an endoscope; an ablation treatment tool; an overtube; a first operation member that is provided at a base end portion of the overtube; and a second operation member that is attachable to and detachable from an intermediate position in a longitudinal direction of an insertion portion of the endoscope. The overtube has a balloon that is configured to fix the overtube to the gastro-intestinal tract; the insertion portion and the ablation treatment tool can be integrally moved in the overtube in the longitudinal direction; and the first and second operation members each have a finger holder that holds at least one finger of one hand. The first operation member is distinct from the overtube, and is attachable to and detachable from an outer circumferential surface of the overtube, at an arbitrary position in the longitudinal direction of the overtube.

8 Claims, 14 Drawing Sheets

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00494* (2013.01); *A61B 2018/00577* (2013.01); *A61B 2018/00982* (2013.01)

(56) References Cited

U.S. PATENT DOCUMENTS

| | | | |
|---|---|---|---|
| 2009/0216081 A1 | 8/2009 | Suzuki et al. | |
| 2009/0247827 A1* | 10/2009 | Secrest | A61B 1/0014 |
| | | | 600/131 |
| 2013/0090526 A1 | 4/2013 | Suzuki et al. | |

FOREIGN PATENT DOCUMENTS

| | | |
|---|---|---|
| JP | 2003-284722 A | 10/2003 |
| JP | 2005-230082 A | 9/2005 |
| JP | 2011-072413 A | 4/2011 |
| JP | 2011-177420 A | 9/2011 |
| JP | 2011-200403 A | 10/2011 |
| JP | 2016-034396 A | 3/2016 |
| JP | 2016-150229 A | 8/2016 |

* cited by examiner

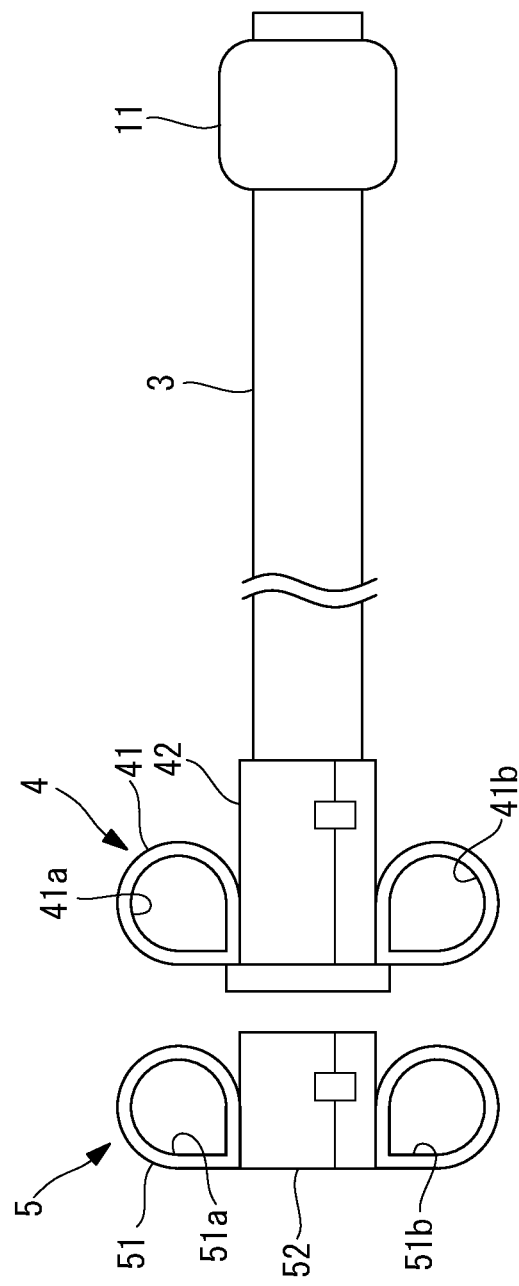

GASTRO-INTESTINAL-TRACT ABLATION SYSTEM

CROSS-REFERENCE TO RELATED APPLICATIONS

This is a continuation of International Application PCT/JP2018/016143, with an international filing date of Apr. 19, 2018, which is hereby incorporated by reference herein in its entirety.

TECHNICAL FIELD

The present invention relates to a gastro-intestinal-tract ablation system.

BACKGROUND ART

Conventionally, when a gastro-intestinal endoscope is inserted into the gastro-intestinal tract through an overtube disposed in the gastro-intestinal tract, the operation of the endoscope and the overtube is manually performed by an operator. There is a known auxiliary equipment for facilitating usability of the endoscope and the overtube performed by an operator (for example, see Patent Literatures 1 and 2). Patent Literature 1 discloses an assisting grip attached to the outer surface of an insertion portion of an endoscope. Patent Literature 2 discloses a handle provided at a base end portion of an overtube.

CITATION LIST

Patent Literature

{PTL 1} Japanese Unexamined Patent Application, Publication No. 2016-34396
{PTL 2} Japanese Unexamined Patent Application, Publication No. 2011-200403

SUMMARY OF INVENTION

An aspect of the present invention is directed to a gastro-intestinal tract ablation system including: an endoscope having an elongated insertion portion; an elongated ablation treatment tool that applies ablation treatment to mucosal tissue; a tubular overtube that is inserted into the gastro-intestinal tract, and that allows the insertion portion and the ablation treatment tool to pass therethrough; a first operation member that is provided at a base end portion of the overtube; and a second operation member that is attachable to and detachable from an intermediate position in a longitudinal direction of the insertion portion of the endoscope, wherein the overtube has a balloon that is configured to fix the overtube to the gastro-intestinal tract, wherein the insertion portion and the ablation treatment tool can be integrally moved in the overtube in the longitudinal direction with the endoscope, wherein the first operation member has a first finger holder that holds at least one finger of one hand of an operator, wherein the second operation member has a second finger holder that holds, among fingers of the one hand, at least one finger other than the at least one finger held by the first finger holder, and wherein the first operation member is distinct from the overtube, and is attachable to and detachable from an outer circumferential surface of the overtube, at an arbitrary position in the longitudinal direction of the overtube.

BRIEF DESCRIPTION OF DRAWINGS

FIG. 10 is a diagram showing modifications of the first operation member and the second operation member.

DESCRIPTION OF EMBODIMENT

A gastro-intestinal-tract ablation system 100 according to an embodiment of the present invention will be described below with reference to the drawings.

Figure 1:
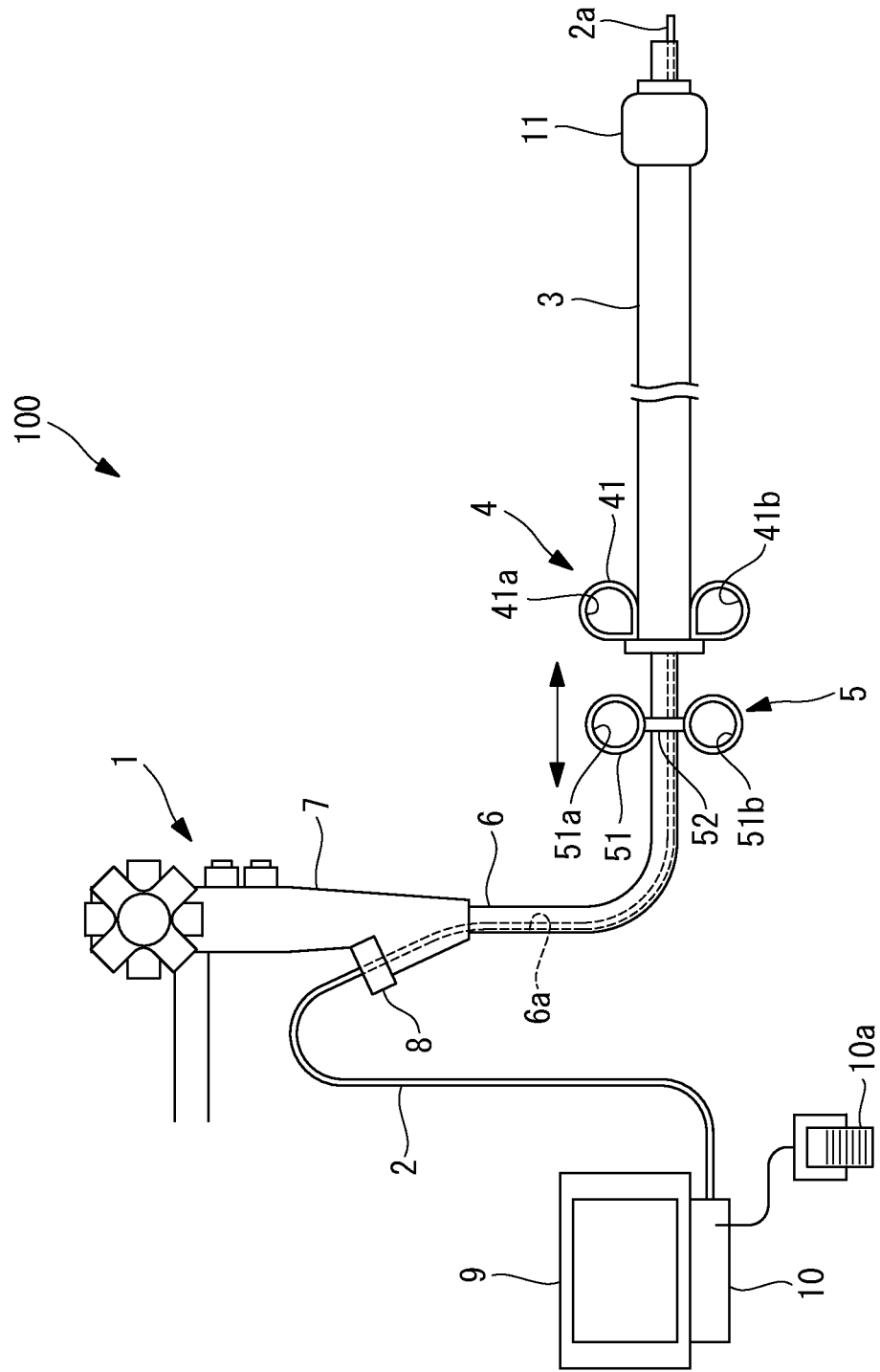
FIG. 1 is an overall configuration diagram of a gastro-intestinal-tract ablation system according to an embodiment of the present invention.
Figure 2:
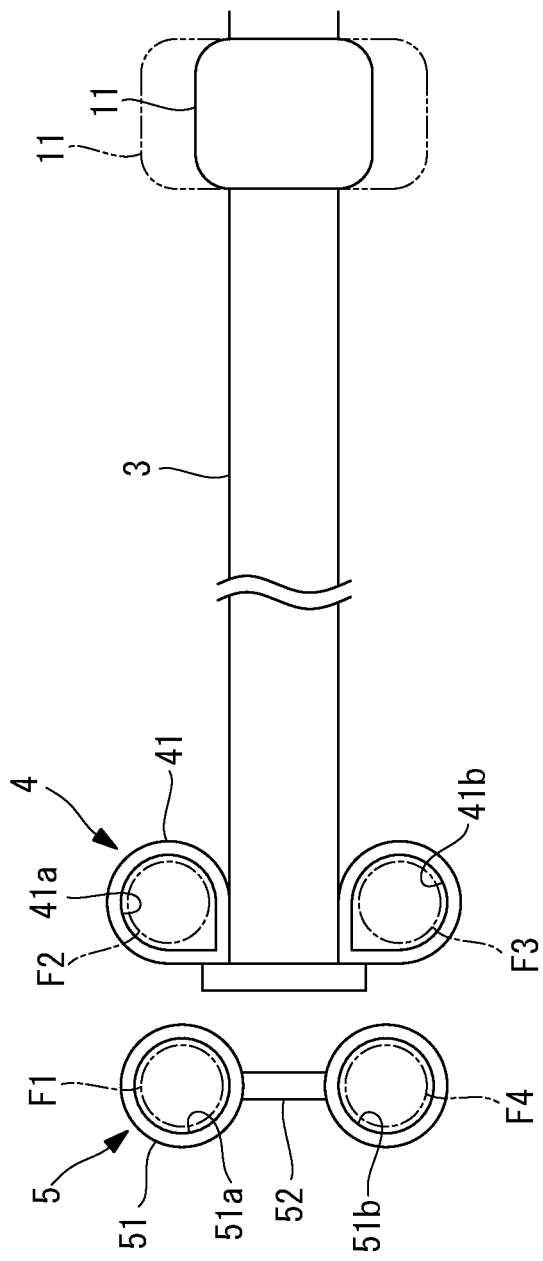
FIG. 2 is a diagram showing an overtube, a first operation member, and a second operation member in the gastro-intestinal-tract ablation system in FIG. 1.

As shown in FIGS. 1 and 2, the gastro-intestinal-tract ablation system 100 according to this embodiment includes: an endoscope 1; an ablation treatment tool 2; an overtube 3; a first operation member 4 that is fixed to a base end portion of the overtube 3; and a second operation member 5 that is attachable to and detachable from the endoscope 1.

The endoscope 1 includes: a flexible, elongated insertion portion 6; and a handle portion 7 that is connected to the base end of the insertion portion 6 and that is for operating a bending portion, etc. of the insertion portion 6. The insertion portion 6 has a treatment-tool channel 6a that penetrates therethrough in the longitudinal direction and into which the ablation treatment tool 2 is inserted. A fixing tool 8 for fixing the ablation treatment tool 2 in the treatment-tool channel 6a to the insertion portion 6 is provided in the vicinity of a base-end opening of the treatment-tool channel 6a. The endoscope 1 is connected to a monitor 9, and an endoscope image acquired by the endoscope 1 is displayed on the monitor 9.

The ablation treatment tool 2 is a flexible, elongated device. The ablation treatment tool 2 applies ablation treatment to the mucous membrane (biological tissue) covering the inner wall of the gastro-intestinal tract by means of energy released from a distal end portion 2a. The energy is, for example, argon plasma, a laser beam, a radio-wave current, a high-frequency current, heat, or ultrasonic waves. The ablation treatment refers to treatment of modifying epithelial cells present in the mucous membrane or removing the epithelial cells from the mucous membrane.

The ablation treatment tool 2 may be a non-contact type that applies the ablation treatment to the mucous membrane in a state in which the distal end portion 2a is separated from the mucous membrane, or a contact type that applies the ablation treatment to the mucous membrane in a state in which the distal end portion 2a is in contact with the mucous membrane.

In the case of a non-contact type, argon plasma or a laser beam is emitted from the distal end portion 2a.

In the case of a contact type, a radio-wave current, a high-frequency current, heat, or ultrasonic waves are released from the distal end portion 2a. The energy is released from, for example, an electrode or an ultrasonic vibrator provided on the surface of a balloon or a plate, or is released from a rake-type or wire-type electrode.

The ablation treatment tool 2 is connected to a controller 10 and is controlled by the controller 10. A foot pedal 10a is connected to the controller 10. An operator can control the output start and the output stop of the energy from the ablation treatment tool 2 by operating the foot pedal 10a with a foot.

The overtube 3 is a flexible, elongated circular tube member and has an inner diameter larger than the outer diameter of the insertion portion 6. The insertion portion 6 can pass through the overtube 3 along the longitudinal direction, and the insertion portion 6 and the overtube 3 can be relatively moved in the longitudinal direction. The overtube 3 has, at a distal end portion thereof, a balloon (fixing portion) 11 for fixing the overtube 3 to the gastro-intestinal tract. The balloon 11 surrounds the outer circumferential surface of the overtube 3 over the entire circumference thereof, and can expand and contract in the radial direction of the overtube 3. The expansion and contraction of the balloon 11 are controlled by supplying a fluid into the balloon 11 and discharging the fluid therefrom via a flow path (not shown) provided in the overtube 3.

As shown in FIG. 2, the first operation member 4 has a finger holding portion (first finger holder) 41 that is fixed to the outer circumferential surface of the base end portion of the overtube 3 and that holds two fingers F2, F3 of one hand of the operator.

The finger holding portion 41 is composed of a pair of annular members and has two holes 41a, 41b into which the fingers F2, F3 can be respectively inserted. The two holes 41a, 41b are provided at two positions where the overtube 3 is sandwiched therebetween in the radial plane perpendicular to the longitudinal direction. In addition, the two holes 41a, 41b open in a direction perpendicular to the longitudinal direction of the overtube 3 and the opposing direction of the two holes 41a, 41b, and the fingers F2, F3 are respectively inserted into the two holes 41a, 41b in the direction perpendicular to the longitudinal direction of the overtube 3. The two fingers F2, F3 inserted into the two holes 41a, 41b are placed substantially parallel to each other at positions where the overtube 3 is sandwiched therebetween in the radial plane perpendicular to the longitudinal direction, and are hooked on the finger holding portion 41 in the longitudinal direction of the overtube 3.

The second operation member 5 has: a finger holding portion (second finger holder) 51 that holds two fingers F1, F4 of one hand of the operator; and an attachment portion 52 that is attached to the outer circumferential surface of the insertion portion 6 so as to be coaxial with the insertion portion 6.

The attachment portion 52 is an annular member mating with the outer circumferential surface of the insertion portion 6. The attachment position of the attachment portion 52 can be changed to an arbitrary position in the longitudinal direction of the insertion portion 6 by inserting the insertion portion 6 into the attachment portion 52 and moving the attachment portion 52 with respect to the insertion portion 6 along the longitudinal direction of the insertion portion 6. The attachment portion 52 is fixed to the outer circumferential surface of the insertion portion 6 by means of friction between the inner circumferential surface of the attachment portion 52 and the outer circumferential surface of the insertion portion 6.

The finger holding portion 51 is composed of a pair of annular members and has two holes 51a, 51b into which the fingers F1, F4 can be respectively inserted. The two holes 51a, 51b are provided at two positions where the attachment portion 52 and the insertion portion 6 are sandwiched therebetween in the radial plane perpendicular to the longitudinal direction. In addition, the two holes 51a, 51b open in a direction perpendicular to the longitudinal direction of the insertion portion 6 and the opposing direction of the two holes 51a, 51b, and the fingers F1, F4 are respectively inserted into the two holes 51a, 51b in the direction perpendicular to the longitudinal direction of the insertion portion 6. The two fingers F1, F4 inserted into the two holes 51a, 51b are placed substantially parallel to each other at positions where the attachment portion 52 and the insertion portion 6 are sandwiched therebetween in the radial plane perpendicular to the longitudinal direction, and are hooked on the finger holding portion 51 in the longitudinal direction of the insertion portion 6.

Next, the operation of the thus-configured gastro-intestinal-tract ablation system 100 will be described.

Figure 3:
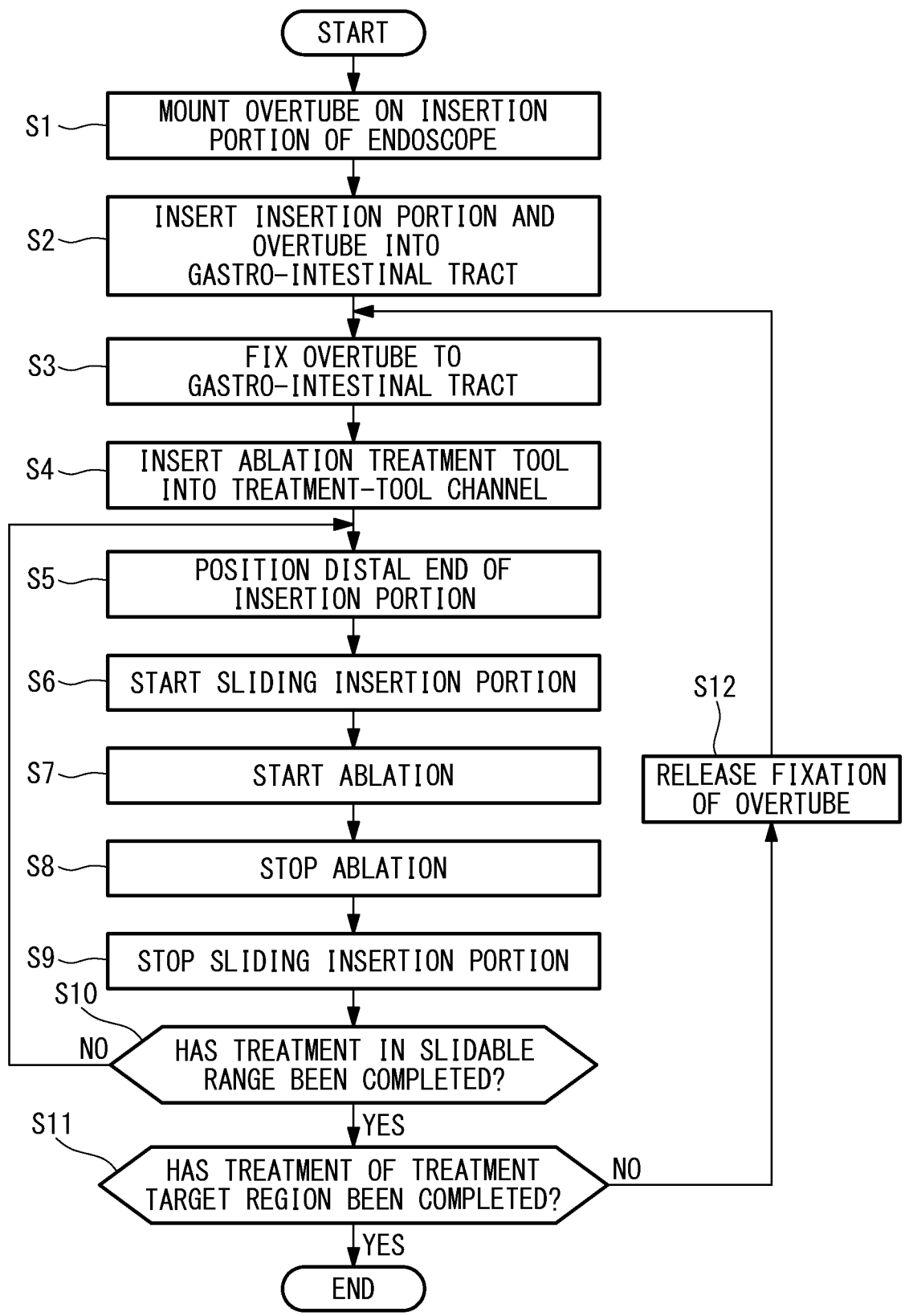
FIG. 3 is a flowchart showing the procedure for treating the mucous membrane of the gastro-intestinal tract by using the gastro-intestinal-tract ablation system in FIG. 1.

FIG. 3 shows the procedure for treating the mucous membrane of the gastro-intestinal tract X by using the gastro-intestinal-tract ablation system 100.

First, the second operation member 5 is attached at an intermediate position in the longitudinal direction of the insertion portion 6, and the insertion portion 6 is made to pass through the overtube 3 to mount the overtube 3 on the outside of the insertion portion 6 (step S1). The second operation member 5 is disposed closer to the base end than the overtube 3 is.

Next, the insertion portion 6 and the overtube 3 are inserted into the gastro-intestinal tract X (for example, the intestinal tract) of a patient (step S2). Because the distal end of the insertion portion 6 protrudes from the distal end of the overtube 3, it is possible to observe the mucous membrane covering the inner surface of the gastro-intestinal tract X in an endoscope image on the monitor 9. The insertion portion 6 and the overtube 3 are disposed at a position where a treatment target region is observed in the endoscope image. At this time, an operator holds and operates the handle portion 7 of the endoscope 1 with one hand (for example, the left hand), and holds and operates the overtube 3 and the insertion portion 6 with the other hand (for example, the right hand).

Figure 4A:
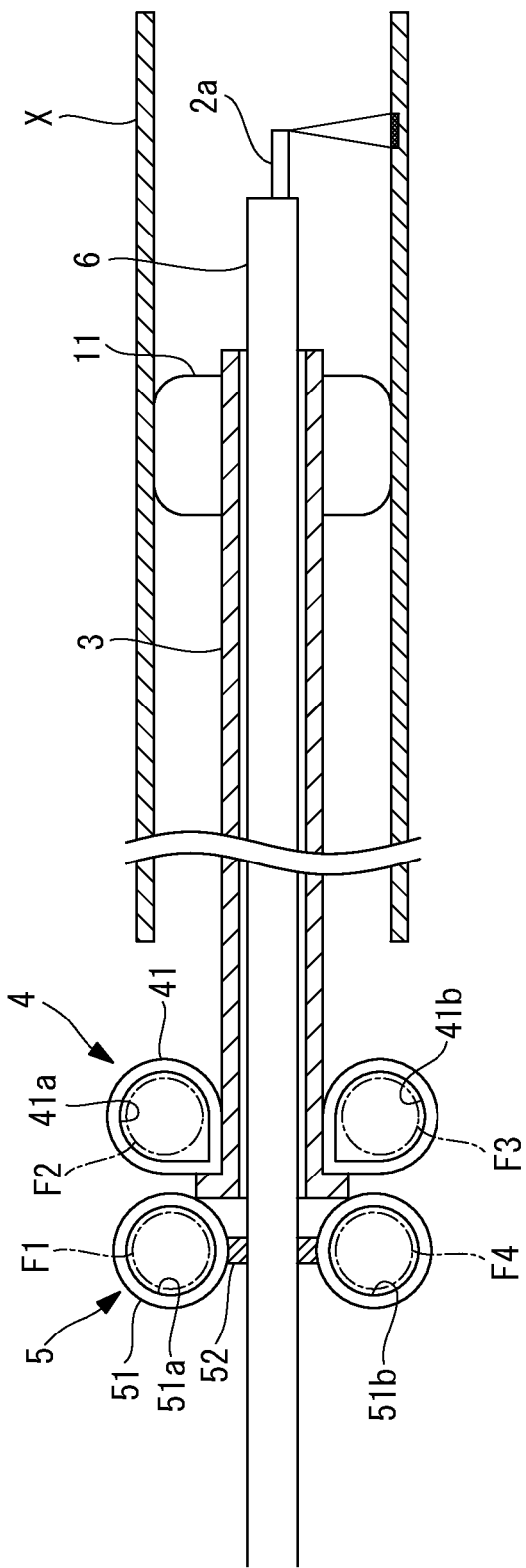
FIG. 4A is a diagram for explaining the operation of the gastro-intestinal-tract ablation system in FIG. 1.

Next, as shown in FIG. 4A, the balloon 11 is expanded (step S3). As a result of the expanded balloon 11 being brought into close contact with the inner wall of the gastro-intestinal tract X and fixed to the inner wall, the overtube 3 is fixed to the gastro-intestinal tract X.

Next, the ablation treatment tool 2 is made to pass through the treatment-tool channel 6a, and the distal end portion 2a is protruded from a distal-end opening of the treatment-tool channel 6a (step S4). Then, the ablation treatment tool 2 is disposed at a position where the distal end portion 2a is observed in the endoscope image, and the insertion portion 6 and the ablation treatment tool 2 are fixed to each other by means of the fixing tool 8. By doing so, it is possible to move the ablation treatment tool 2 in the treatment-tool channel 6a integrally with the insertion portion 6 in the overtube 3, while constantly observing the distal end portion 2a with the endoscope 1.

Next, the insertion portion 6 and the ablation treatment tool 2 are integrally advanced with respect to the overtube 3, the distal end of the insertion portion 6 is disposed at a position separated from the distal end of the overtube 3, and the distal end of the insertion portion 6 is positioned with respect to the mucous membrane (step S5).

Next, sliding of the insertion portion 6 and the ablation treatment tool 2 with respect to the overtube 3 is started (step S6).

Specifically, as shown in FIG. 4A, the second operation member 5 is disposed at a position at which the second operation member 5 abuts against the base end of the overtube 3. Next, as shown in FIG. 2, the index finger F2 and the middle finger F3 of the other hand (for example, the right hand) are inserted into the two holes 41a, 41b of the first operation member 4, and the thumb F1 and the ring finger F4 of the other hand (for example, the right hand) are inserted into the two holes 51a, 51b of the second operation member 5. Next, the thumb F1 and the ring finger F4 are slowly moved with respect to the index finger F2 and the middle finger F3 in a separating direction. Because the overtube 3 is fixed to the gastro-intestinal tract X, by moving the thumb F1 and the ring finger F4, the insertion portion 6 and the ablation treatment tool 2 are slid toward the base end with respect to the overtube 3.

Figure 4B:
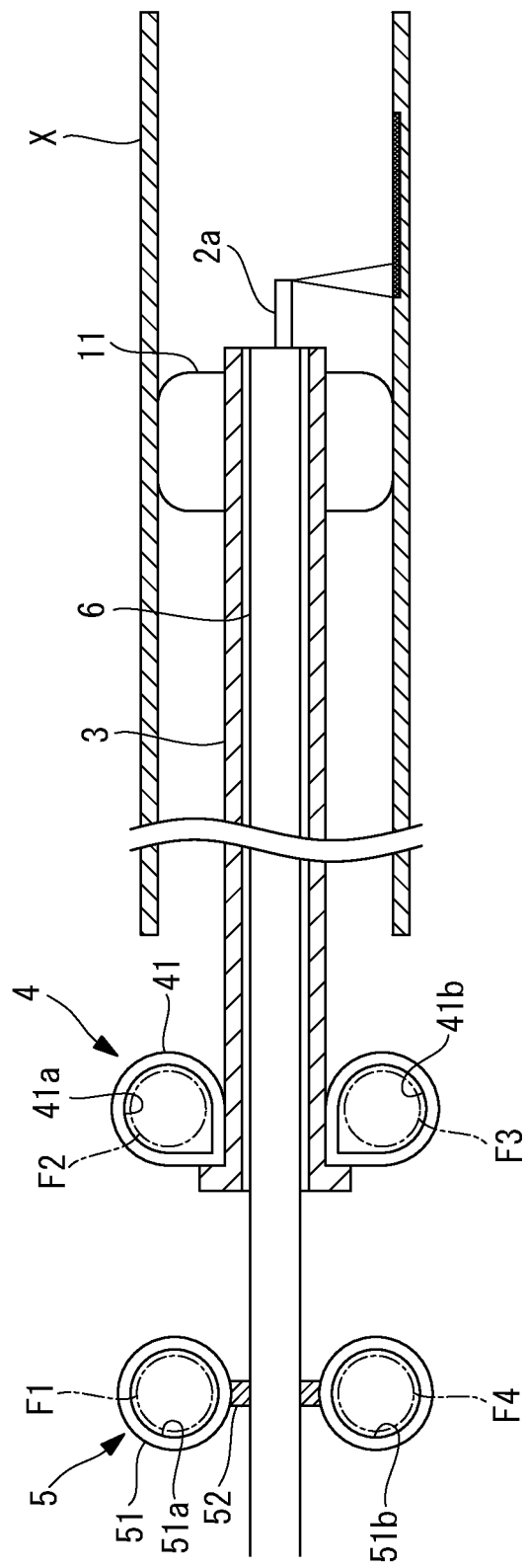
FIG. 4B is a diagram for explaining the operation of the gastro-intestinal-tract ablation system in FIG. 1.

After starting sliding of the insertion portion 6 and the ablation treatment tool 2 in step S6, the energy output from the ablation treatment tool 2 is started by operating the foot pedal 10a (step S7). By doing so, as shown in FIG. 4B, the mucous membrane is continuously treated by means of the energy released from the distal end portion 2a, while the distal end portion 2a is slid toward the base end. At this time, the insertion portion 6 is also moved integrally with the distal end portion 2a; thus, the operator can constantly observe a region treated by the distal end portion 2a in the endoscope image.

The distance (stroke) by which the operator can slide the ablation treatment tool 2 at a time is determined by the movable range of the fingers of the operator. When the ablation treatment tool 2 has moved to the vicinity of the end of the stroke, the energy output from the ablation treatment tool 2 is stopped (step S8), and subsequently, the sliding operation of the insertion portion 6 and the ablation treatment tool 2 is ended (step S9).

The ablation treatment tool 2 can be slid to a position where the distal end portion 2a is disposed in the vicinity of the distal end of the overtube 3. In the case in which the ablation treatment of the mucous membrane in the entire slidable range of the ablation treatment tool 2 has not been completed yet (NO in step S10), steps S5 to S9 are repeated.

After the ablation treatment of the mucous membrane in the entire slidable range of the ablation treatment tool 2 is completed (YES in step S10), the fixation of the overtube 3 to the gastro-intestinal tract X is released by contracting the balloon 11 (step S12). Next, the position of the overtube 3 is changed, and steps S3 to S10 are repeated.

Steps S3 to S10 and S12 are repeated until the ablation treatment of the entire treatment target region is completed (YES in step S11).

Figure 5A:
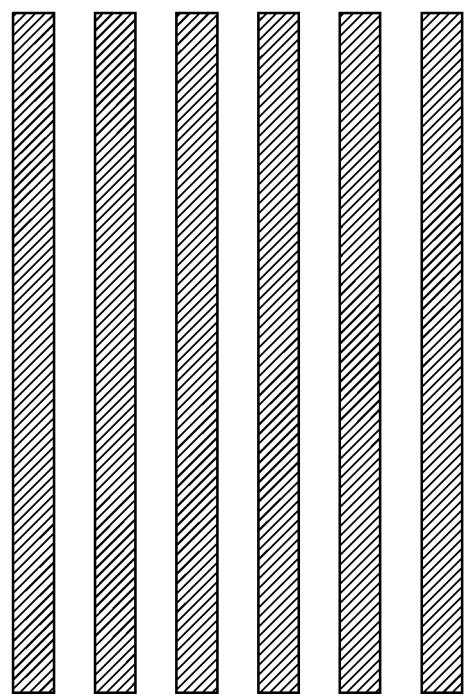
FIG. 5A is a diagram showing treatment regions when the ablation treatment has been applied to the mucous membrane while sliding an insertion portion and an ablation treatment tool.
Figure 5B:
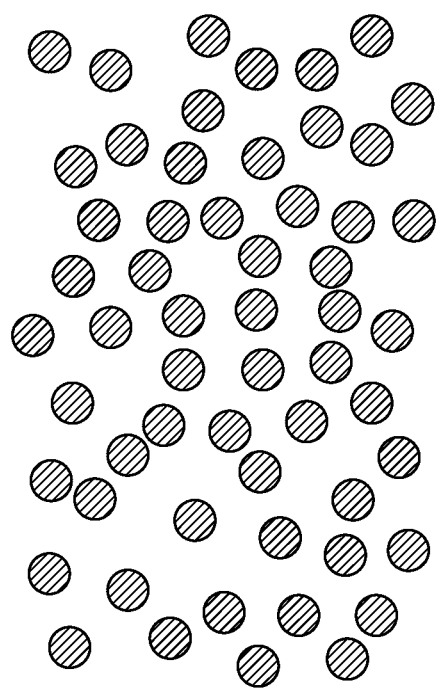
FIG. 5B is a diagram showing treatment regions when the ablation treatment has been applied to the mucous membrane without sliding the insertion portion and the ablation treatment tool.

FIG. 5A shows treatment regions when the mucous membrane has been treated while sliding the ablation treatment tool 2. FIG. 5B shows treatment regions when the mucous membrane has been treated without sliding the ablation treatment tool 2.

As shown in FIG. 5B, in the case in which the ablation treatment tool 2 is not slid, it is necessary to treat a number of small ranges while repeatedly changing the position of the ablation treatment tool 2 in order to treat a wide range of the mucous membrane.

On the contrary, as shown in FIG. 5A, in the case in which the ablation treatment tool 2 is slid, a wide linear range is treated with a single slide.

As described above, with this embodiment, the overtube 3 is provided with the balloon 11 that fixes the overtube 3 to the gastro-intestinal tract X. In addition, the overtube 3 and the insertion portion 6 are respectively provided with the finger holding portions 41, 51 that hold the fingers of one hand. Therefore, there is an advantage in that it is possible to easily slide the insertion portion 6 and the ablation treatment tool 2 with respect to the overtube 3, in a state in which the overtube 3 is fixed to the gastro-intestinal tract X by means of the balloon 11, by movements of the four fingers F1, F2, F3, F4 of one hand, which are held by the finger holding portions 41, 51.

In addition, sliding of the insertion portion 6 and the ablation treatment tool 2 is controlled by the movements of the fingers F1, F2, F3, F4 of the operator; thus, the operator can easily slide the insertion portion 6 and the ablation treatment tool 2 at a constant low speed. By doing so, there is an advantage in that it is possible to treat a wide range of the mucous membrane in a reliable and uniform manner.

Figure 6:
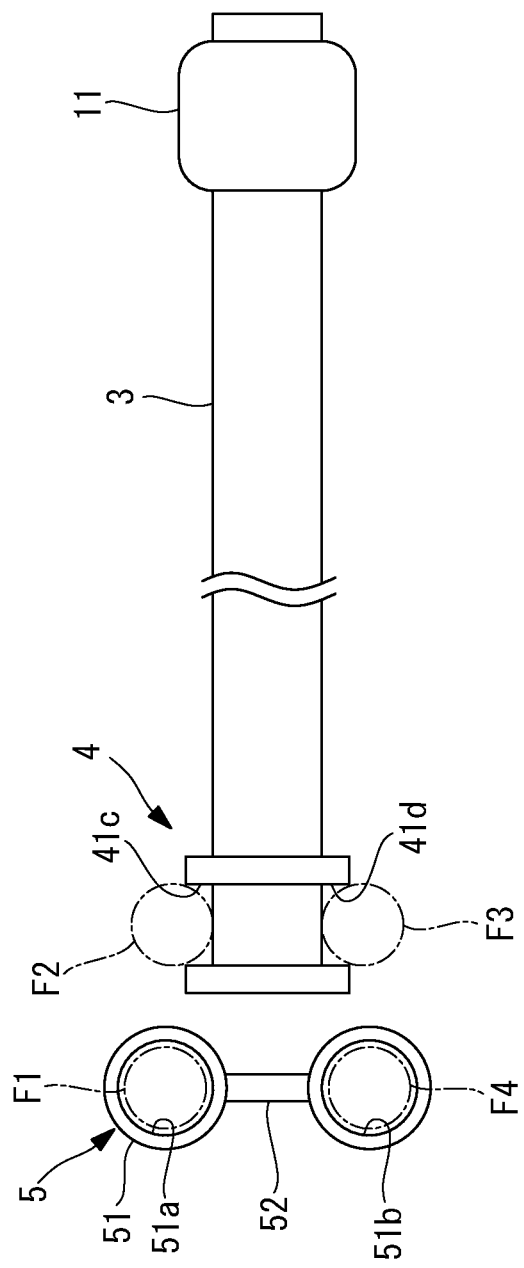
FIG. 6 is a diagram showing a modification of a finger holding portion of the first operation member.

Although the first finger holding portion 41 has the holes 41a, 41b into which the fingers F2, F3 are inserted in this embodiment, alternatively, as shown in FIG. 6, the first finger holding portion 41 may have recessed portions 41c, 41d that receive side surfaces of the fingers F2, F3. The recessed portions 41c, 41d extend in a direction perpendicular to the longitudinal direction of the overtube 3, and the fingers F2, F3 are respectively placed in the direction perpendicular to the longitudinal direction of the overtube 3.

Figure 7A:
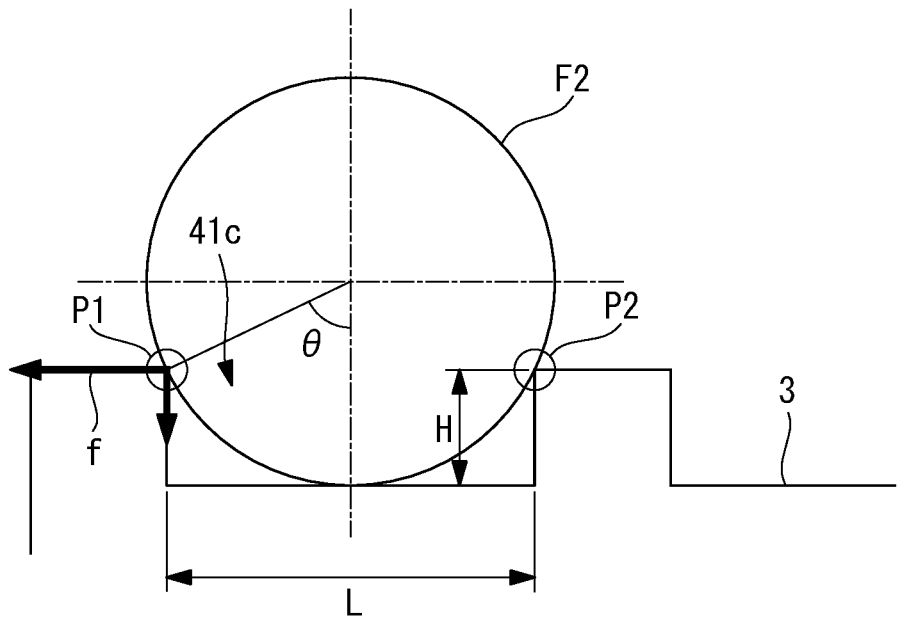
FIG. 7A is a diagram for explaining Conditional Expressions (1) and (2) for the finger holding portion in FIG. 6.

When the insertion portion 6 is slid toward the base end, the balls of the fingers F2, F3 in the recessed portions 41c, 41d get caught by base-end-side inner surfaces of the recessed portions 41c, 41d, and a force acts on the first operation member 4 and the overtube 3. When the insertion portion 6 is slid toward the distal end, the backs of the fingers F2, F3 in the recessed portions 41c, 41d get caught by distal-end-side inner surfaces of the recessed portions 41c, 41d, and a force acts on the first operation member 4 and the overtube 3. As shown in FIG. 7A, the action points P1, P2 in these cases are the outermost ends of the inner surfaces in the radial direction.

It is preferable that the shape of the recessed portion 41c, 41d satisfy Expressions (1) and (2) below.

$$H \geq L/5 \quad (1)$$

$$5 \text{ mm} \leq L \leq 30 \text{ mm} \quad (2)$$

As shown in FIG. 7A, H indicates the height of the action point P1, P2 in the radial direction of the overtube 3 (the distance in the radial direction of the overtube 3 from the bottom surface on the radial inner side of the recessed portion 41c, 41d to the action point P1, P2). L indicates the distance between the two action points P1, P2 in the longitudinal direction of the overtube 3.

As a result of satisfying Expressions (1) and (2), a component f, in the longitudinal direction of the overtube 3, of the force applied to the action point P1, P2 from the finger F2, F3 of the operator becomes large. Therefore, the force applied to the action point P1, P2 is efficiently converted to sliding of the insertion portion 6 and the ablation treatment tool 2 in the longitudinal direction.

Figure 8:
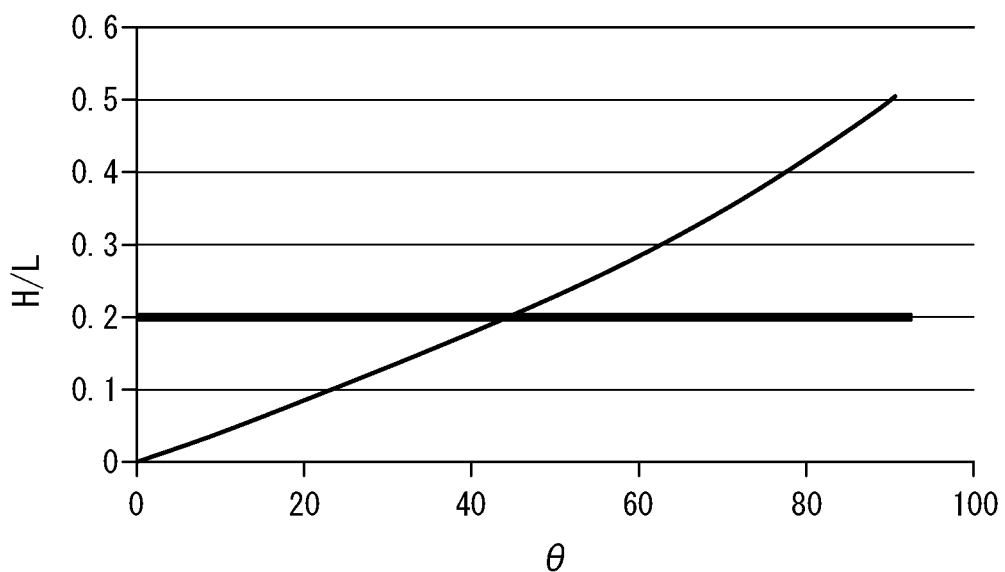
FIG. 8 is a graph representing the relationship between 0 and H/L.

FIG. 8 shows the relationship between H/L (=(1−cos θ)÷2 sin θ) and θ. As shown in FIG. 7A, θ indicates the angle formed between a line segment connecting the central axis of the finger F2 and the action point P1 and a perpendicular line from the central axis of the finger F2 to the bottom surface of the recessed portion 41c. In order to efficiently apply the force in the longitudinal direction of the overtube 3 to the action point P1 from the finger F2, θ is preferably 45° or larger. When H=L/5, θ becomes approximately 45°.

Figure 7B:
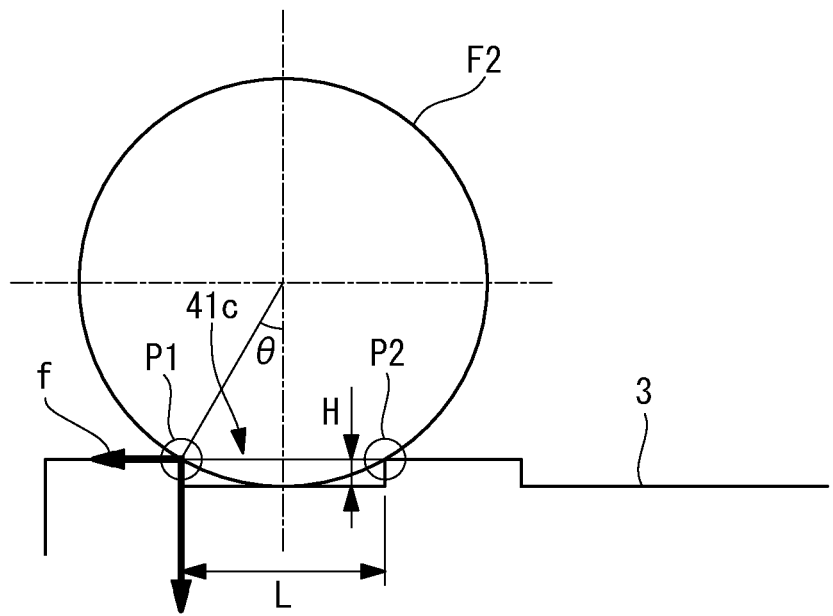
FIG. 7B is a diagram showing a comparative example of the finger holding portion in FIG. 6.

In the case in which θ is smaller than 45°, as shown in FIG. 7B, a component f, in the longitudinal direction of the overtube 3, of the force applied to the action point P1 from the finger F2 becomes small. Therefore, a larger force needs to be applied to the action point P1 to slide the insertion portion 6 and the ablation treatment tool 2 in the longitudinal direction.

Figure 9A:
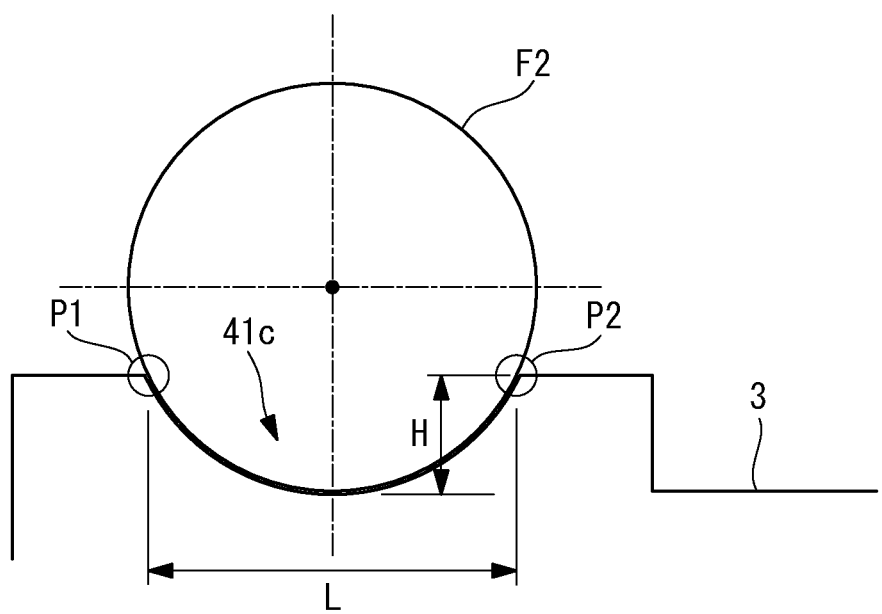
FIG. 9A is a diagram showing another modification of the first finger holding portion.
Figure 9B:
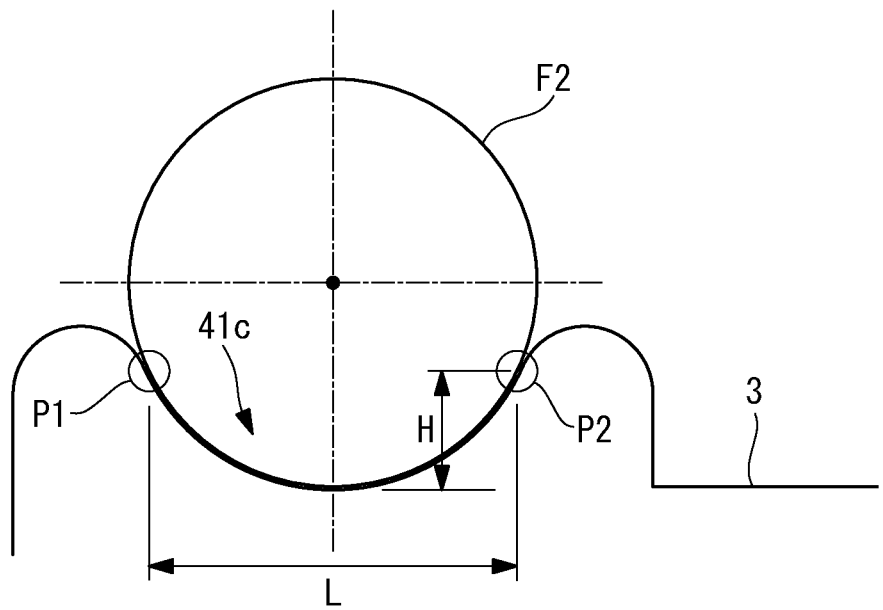
FIG. 9B is a diagram showing another modification of the first finger holding portion.

As shown in FIG. 6, the inner surface of the recessed portion 41c, 41d may be formed of a plurality of planar surfaces that are mutually angled; however, as shown in FIGS. 9A and 9B, the inner surface of the recessed portion 41c, 41d may be a curved surface conforming to the shape of the side surface of the finger F2, F3.

Figure 9C:
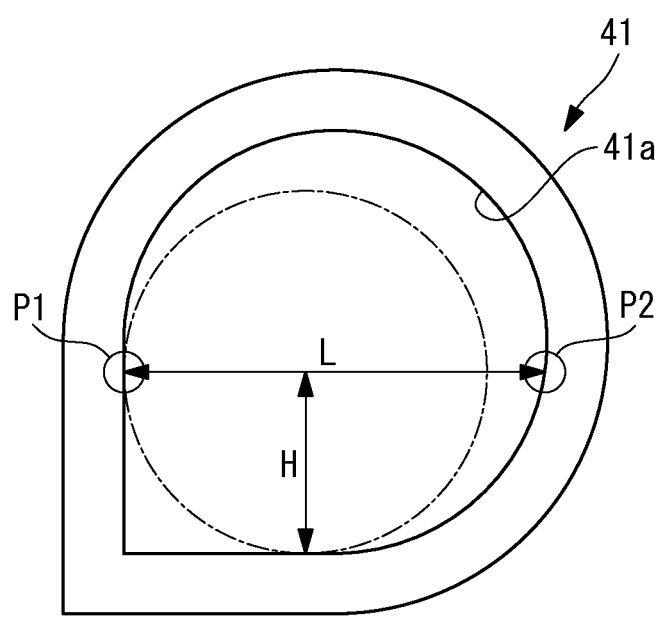
FIG. 9C is a diagram for explaining Conditional Expressions (1) and (2) for the annular first finger holding portion.

As shown in FIG. 9C, it is also preferable that Expressions (1) and (2) be satisfied in the case in which the finger holding portion 41 has the holes 41a, 41b.

Although the first operation member 4 is fixed to the overtube 3 in this embodiment, alternatively, as shown in FIG. 10, the first operation member 4 may be attachable to and detachable from the overtube 3.

The first operation member 4 in FIG. 10 has an attachment portion 42 that is attached to the outer circumferential surface of the base end portion of the overtube 3. The attachment portion 42 is a tubular member mating with the outer circumferential surface of the base end portion of the overtube 3. The attachment portion 42 can be opened and closed in the radial direction, and can be mated with the base end portion of the overtube 3 in the radial direction. Similar to the attachment portion 42, the attachment portion 52 of the second operation member 5 in FIG. 10 can also be opened and closed in the radial direction, and can be mated with the insertion portion 6 in the radial direction.

Figure 11:
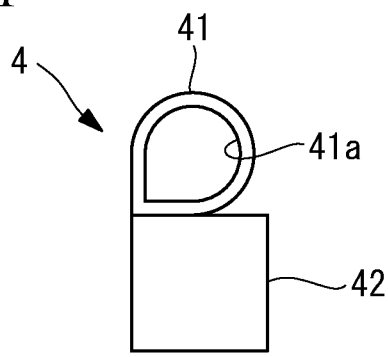
FIG. 11 is a diagram showing another modification of the first operation member.

Although the first finger holding portion 41 holds the two fingers F2, F3 by means of the two holes 41a, 41b in this embodiment, alternatively, as shown in FIG. 11, the first finger holding portion 41 may be configured to have only one hole 41a and to hold only one finger.

Figure 12:
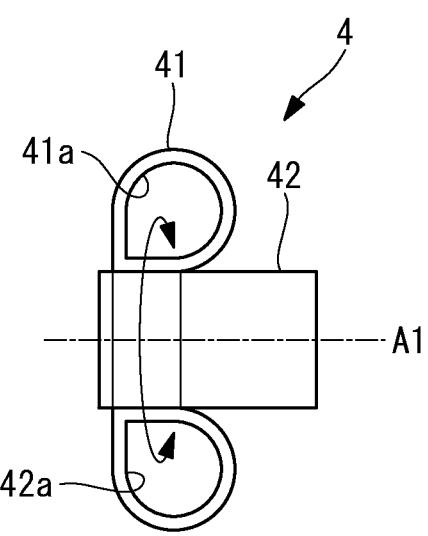
FIG. 12 is a diagram showing another modification of the first operation member.

In this embodiment, as shown in FIG. 12, the finger holding portion 41 may be rotatable about a longitudinal axis A1 of the overtube 3.

By rotating the finger holding portion 41 about the longitudinal axis A1, it is possible to change the positions of the holes 41a, 41b to positions where the fingers F2, F3 are easily inserted thereinto, while the orientation of the overtube 3 about the longitudinal axis A1 is kept constant.

Similarly, the finger holding portion 51 may be rotatable about a longitudinal axis of the insertion portion 6.

Figure 13:
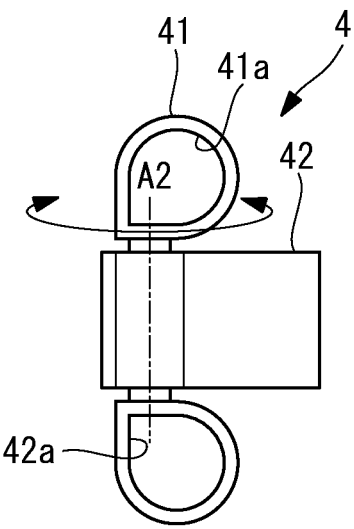
FIG. 13 is a diagram showing another modification of the first operation member.

In this embodiment, as shown in FIG. 13, the finger holding portion 41 may be rotatable about an axis A2 in the radial direction of the overtube 3.

By rotating the finger holding portion 41 about the axis A2, it is possible to change the orientations of the holes 41a, 41b to orientations in which the fingers F2, F3 are easily inserted thereinto, while the position of the overtube 3 is kept constant.

Similarly, the finger holding portion 51 may be rotatable about an axis in the radial direction of the insertion portion 6.

Figure 14:
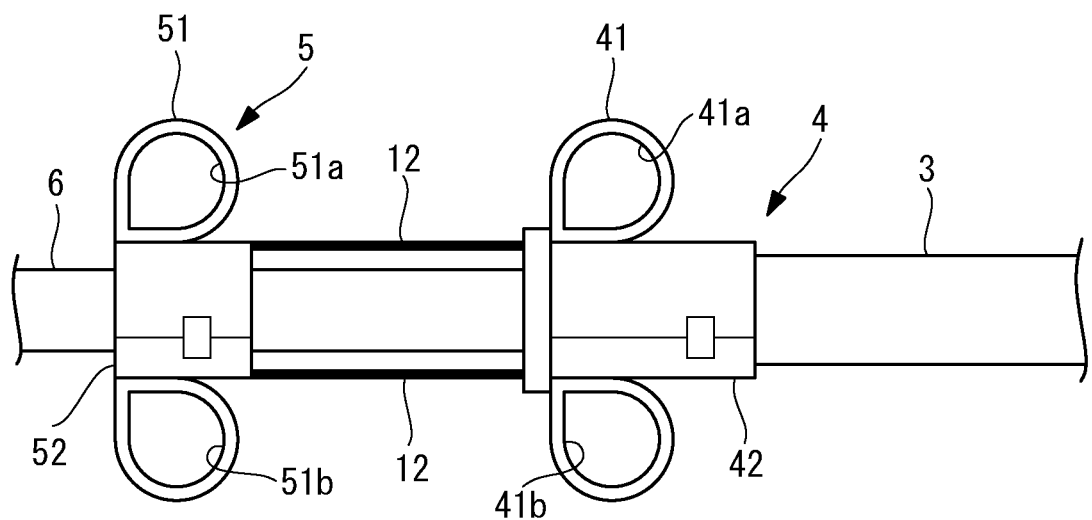
FIG. 14 is a diagram showing an example of a restriction member provided on the first operation member and the second operation member.

In this embodiment, as shown in FIG. 14, a restriction member 12 that restricts the distance between the first operation member 4 and the second operation member 5 in the longitudinal direction of the overtube 3 to a desired distance or less may be provided.

The restriction member 12 is, for example, a flexible member that connects the first operation member 4 and the second operation member 5 and has a fixed length. With this configuration, the movable range of the second operation member 5 with respect to the first operation member 4 is restricted, and it is possible to prevent the insertion portion 6 and the ablation treatment tool 2 from sliding excessively toward the base end.

Figure 15:
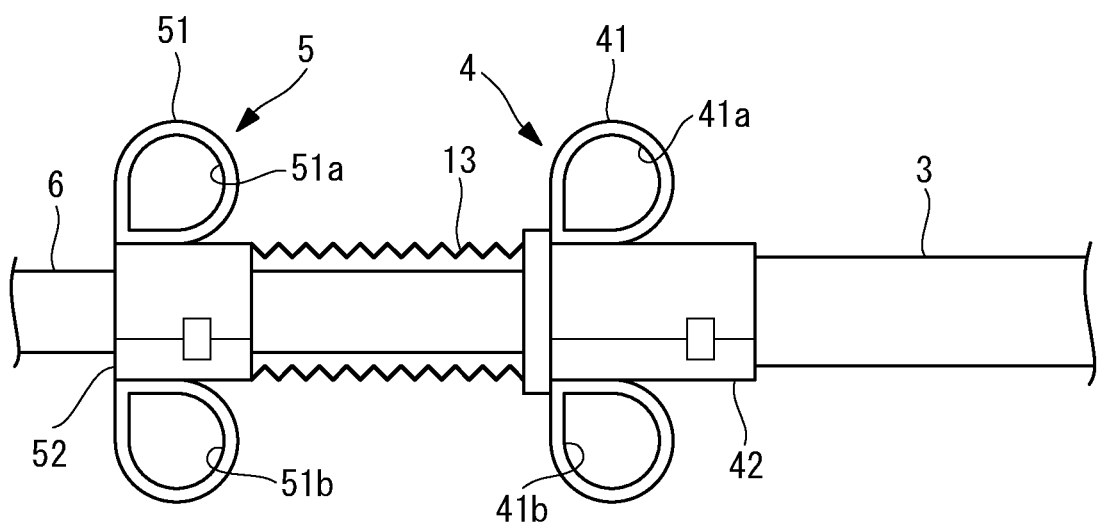
FIG. 15 is a diagram showing an example of an elastic member provided on the first operation member and the second operation member.

In this embodiment, as shown in FIG. 15, an elastic member 13 that detaches the first operation member 4 and the second operation member 5 in a mutually separating direction may be provided. The elastic member 13 is, for example, a spring that is disposed between the two operation members 4, 5 and that connects the two operation members 4, 5.

The operation of sliding the insertion portion 6 and the ablation treatment tool 2 toward the base end, which is performed by the operator, is assisted by the elastic force of the elastic member 13. Therefore, the operator can slide the insertion portion 6 and the ablation treatment tool 2 toward the base end with a smaller force.

Figure 16:
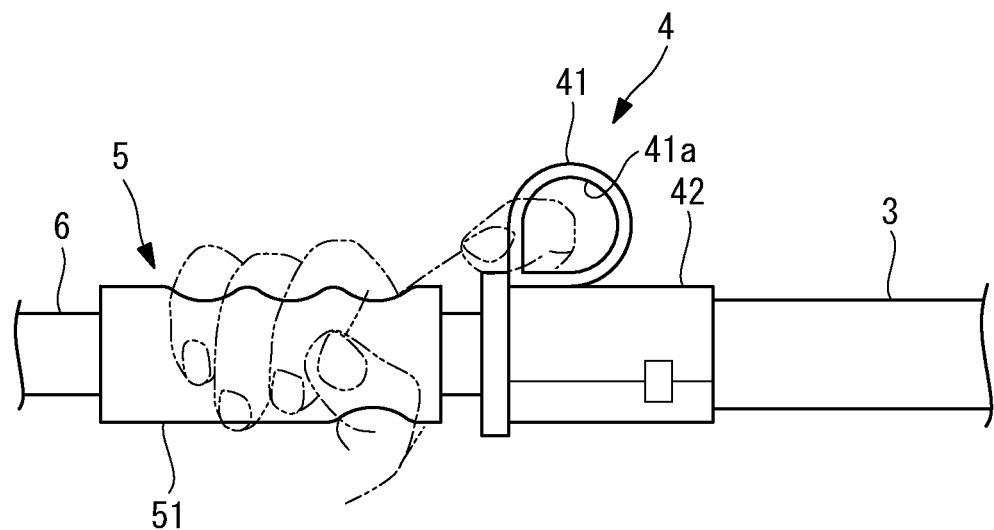
FIG. 16 is a diagram showing another modification of the second operation member.
Figure 17:
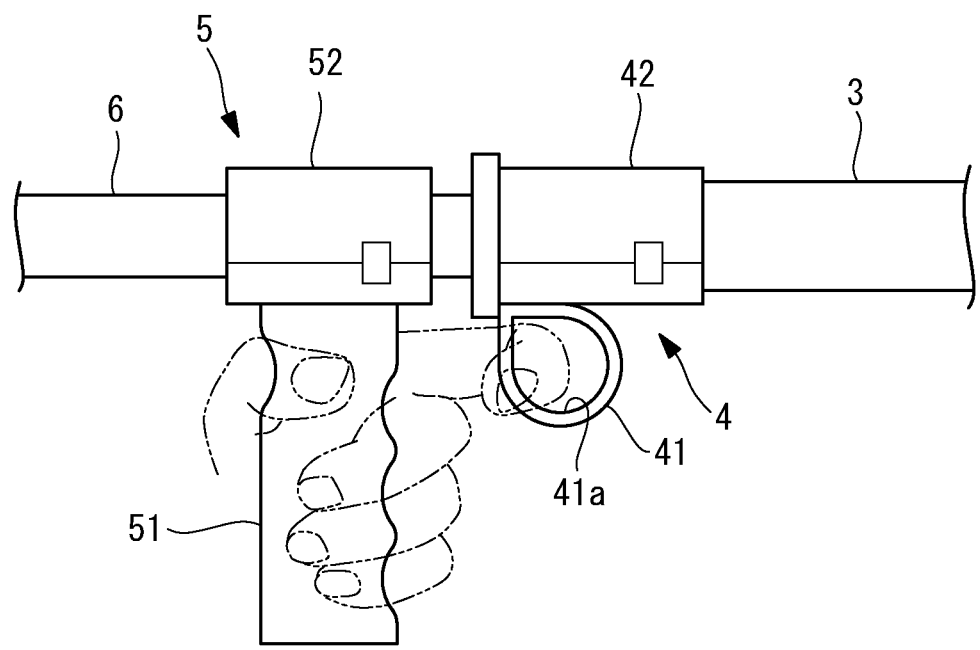
FIG. 17 is a diagram showing another modification of the second operation member.

Although the second finger holding portion 51 has the two holes 51a, 51b into which the fingers F1, F4 are inserted in this embodiment, alternatively, as shown in FIGS. 16 and 17, a grip that is held with one hand may be provided.

The grip 51 is configured to be held with, among the five fingers of one hand, the fingers other than the finger held by the first finger holding portion 41.

Although the elongated ablation treatment tool 2 that is distinct from the endoscope 1 is provided in this embodiment, alternatively, an ablation treatment tool may be fixed to the distal end of the insertion portion 6.

As a result, the above-described embodiment leads to the following aspect.

An aspect of the present invention is directed to a gastrointestinal-tract ablation system including: an endoscope having an elongated insertion portion; an elongated ablation treatment tool that applies ablation treatment to biological tissue; a tubular overtube that is inserted into the gastro-intestinal tract, and that allows the insertion portion and the ablation treatment tool to pass therethrough; a first operation member that is provided at a base end portion of the overtube; and a second operation member that is attachable to and detachable from an intermediate position in a longitudinal direction of the insertion portion. The overtube has a fixing portion that fixes the overtube to the gastro-intestinal tract; the insertion portion and the ablation treatment tool can be integrally moved in the overtube in the longitudinal direction; the first operation member has a first finger holding portion that holds at least one finger of one hand of an operator; and the second operation member has a second finger holding portion that holds, among fingers of the one hand, at least one finger other than the at least one finger held by the first finger holding portion.

With this aspect, the insertion portion of the endoscope and the ablation treatment tool are made to pass through the overtube disposed in the gastro-intestinal tract. Subsequently, ablation treatment of the mucous membrane covering the inner surface of the gastro-intestinal tract is continuously performed by means of the ablation treatment tool, while the insertion portion and the ablation treatment tool are slid in the longitudinal direction with respect to the overtube. By doing so, it is possible to efficiently treat a wide range of the mucous membrane while observing the mucous membrane to be treated with the endoscope.

In this case, the operator fixes the overtube to the gastro-intestinal tract by means of the fixing portion, places the fingers of one hand such that at least one finger is held by each of the first operation member provided on the overtube and the second operation member attached to the insertion portion, and moves the finger in the first finger holding portion and the finger in the second finger holding portion in a mutually separating or approaching direction. By doing so, by using only one hand, it is possible to easily slide the insertion portion and the ablation treatment tool with respect to the overtube fixed to the gastro-intestinal tract.

In addition, the operator can easily control the sliding speed of the insertion portion and the ablation treatment tool by the movement of his/her own fingers. Therefore, it is possible to slide the insertion portion and the ablation treatment tool at a constant low speed, and to treat the inner wall of the gastro-intestinal tract in a uniform and reliable manner.

In the abovementioned aspect, the insertion portion may have a treatment-tool channel that allows the ablation treatment tool to pass therethrough.

With this configuration, it is possible to use an endoscope and an ablation treatment tool that are distinct from each other.

In the abovementioned aspect, the first operation member may be distinct from the overtube, and may be attachable to and detachable from an outer circumferential surface of the overtube, at an arbitrary position in the longitudinal direction of the overtube.

With this configuration, it is possible to use a general overtube.

In the abovementioned aspect, the first finger holding portion may have a hole into which the finger is inserted in a direction perpendicular to the longitudinal direction of the overtube.

The finger inserted into the hole of the first finger holding portion is placed in a direction perpendicular to the longitudinal direction of the overtube, and is hooked in the longitudinal direction of the first finger holding portion and the overtube. By doing so, it is possible to stably hold the finger with respect to the overtube.

In the abovementioned aspect, the second finger holding portion may have a hole into which the finger is inserted in a direction perpendicular to the longitudinal direction of the insertion portion.

The finger inserted into the hole of the second finger holding portion is placed in a direction perpendicular to the longitudinal direction of the insertion portion, and is hooked in the longitudinal direction of the second finger holding portion and the insertion portion. By doing so, it is possible to stably hold the finger with respect to the insertion portion.

In the abovementioned aspect, the first operation member may have the two first finger holding portions, and the two first finger holding portions may be provided at two positions where the overtube is sandwiched therebetween in a radial direction.

With this configuration, two fingers held by the two first finger holding portions are placed at positions where the overtube is sandwiched therebetween in the radial direction. By doing so, it is possible to hold the two fingers with respect to the overtube in a more stable manner.

In the abovementioned aspect, the second operation member may have the two second finger holding portions, and the two second finger holding portions may be provided at two positions where the insertion portion is sandwiched therebetween in the radial direction.

With this configuration, two fingers held by the two second finger holding portions are placed at positions where the insertion portion is sandwiched therebetween in the radial direction. By doing so, it is possible to hold the two fingers with respect to the insertion portion in a more stable manner.

In the abovementioned aspect, a restriction member that restricts a distance between the first operation member and the second operation member in the longitudinal direction of the overtube to a desired distance or less may be provided.

With this configuration, it is possible to restrict the movable range of the second operation member with respect to the first operation member, and to prevent the insertion portion and the ablation treatment tool from sliding excessively toward the base end.

In the abovementioned aspect, an elastic member that detaches the first operation member and the second operation member in a mutually separating direction may be provided.

With this configuration, the operation of sliding the insertion portion and the ablation treatment tool toward the base end is assisted by the elastic force of the elastic member. Therefore, the operator can slide the insertion portion and the ablation treatment tool toward the base end with a smaller force.

The present invention affords an advantage in that it is possible to easily make an endoscope and an ablation treatment tool slide with respect to an overtube by using only one hand.

REFERENCE SIGNS LIST 100 gastro-intestinal-tract ablation system
1 endoscope
2 ablation treatment tool
3 overtube
4 first operation member
41 first finger holding portion
41a, 41b hole 5 second operation member
51 second finger holding portion
51a, 51b hole
52 attachment portion
6 insertion portion
6a treatment-tool channel
7 handle portion
8 fixing tool
9 monitor
10 controller
10a foot pedal
11 balloon (fixing portion)
12 restriction member
13 elastic member
F1, F2, F3, F4 finger

The invention claimed is:

1. A gastro-intestinal-tract ablation system comprising:
an endo scope having an elongated insertion portion;
an elongated ablation treatment tool configured to apply ablation treatment to mucosal tissue;
a tubular overtube that is inserted into the gastro-intestinal tract, and that allows the insertion portion and the ablation treatment tool to pass therethrough;
a first operation member that is provided at a base end portion of the overtube; and
a second operation member that is attachable to and detachable from an intermediate position in a longitudinal direction of the insertion portion of the endoscope,
wherein the overtube has a balloon that is configured to fix the overtube to the gastro-intestinal tract,
wherein the insertion portion and the ablation treatment tool can be integrally moved in the overtube in the longitudinal direction with the endo scope,
wherein the first operation member has a first finger holder configured to hold at least one finger of one hand of an operator,
wherein the second operation member has a second finger holder configured to hold, among fingers of the one hand, at least one finger other than the at least one finger held by the first finger holder, and
wherein the first operation member is distinct from the overtube, and is attachable to and detachable from an outer circumferential surface of the overtube, at an arbitrary position in the longitudinal direction of the overtube.

2. The gastro-intestinal-tract ablation system according to claim 1, wherein the insertion portion has a treatment-tool channel that allows the ablation treatment tool to pass therethrough.

3. The gastro-intestinal-tract ablation system according to claim 1, wherein the first finger holder has a hole configured for insertion of the finger in a direction perpendicular to the longitudinal direction of the overtube.

4. The gastro-intestinal-tract ablation system according to claim 1, wherein the second finger holder has a hole configured for insertion of the finger in a direction perpendicular to the longitudinal direction of the insertion portion.

5. The gastro-intestinal-tract ablation system according to claim 1, wherein the first operation member has the two first finger holders, and the two first finger holders are provided at two positions where the overtube is sandwiched therebetween in a radial plane perpendicular to the longitudinal direction.

6. The gastro-intestinal-tract ablation system according to claim 1, wherein the second operation member has the two second finger holders, and the two second finger holders are provided at two positions where the insertion portion is sandwiched therebetween in a radial plane perpendicular to the longitudinal direction.

7. The gastro-intestinal-tract ablation system according to claim 1, further comprising a restriction member that restricts a distance between the first operation member and the second operation member in the longitudinal direction of the overtube to a desired distance or less.

8. The gastro-intestinal-tract ablation system according to claim 1, further comprising an elastic member that detaches the first operation member and the second operation member in a mutually separating direction.

* * * * *